(12) United States Patent
Zabetian et al.

(10) Patent No.: US 10,249,388 B2
(45) Date of Patent: Apr. 2, 2019

(54) METHODS AND SYSTEMS FOR REPLENISHING SUPPLIES IN A PRODUCT ARRAY

(71) Applicant: CooperVision International Holding Company, LP, St. Michael (BB)

(72) Inventors: Mahboud Zabetian, Orinda, CA (US); Shaun Schooley, Moraga, CA (US)

(73) Assignee: CooperVision International Holding Company, LP, St. Michael (BB)

( * ) Notice: Subject to any disclaimer, the term of this patent is extended or adjusted under 35 U.S.C. 154(b) by 844 days.

(21) Appl. No.: 14/819,379

(22) Filed: Aug. 5, 2015

(65) Prior Publication Data

US 2016/0042138 A1    Feb. 11, 2016

Related U.S. Application Data

(60) Provisional application No. 62/033,449, filed on Aug. 5, 2014.

(51) Int. Cl.
| | |
|---|---|
| *G16H 40/40* | (2018.01) |
| *G06Q 30/06* | (2012.01) |
| *G06F 19/00* | (2018.01) |

(52) U.S. Cl.
CPC .......... *G16H 40/40* (2018.01); *G06F 19/00* (2013.01); *G06Q 30/06* (2013.01)

(58) Field of Classification Search
CPC ..... G16H 40/40; G06Q 30/06; G06F 19/3412
See application file for complete search history.

(56) References Cited

U.S. PATENT DOCUMENTS

| | | | | |
|---|---|---|---|---|
| 7,774,097 | B2* | 8/2010 | Rosenblum | G06F 19/3462 700/236 |
| 2011/0022980 | A1* | 1/2011 | Segal | G06F 3/0488 715/810 |
| 2013/0137607 | A1* | 5/2013 | Ghatak | G01N 33/6854 506/39 |
| 2015/0170095 | A1* | 6/2015 | Chudy | G06Q 10/087 348/143 |

\* cited by examiner

*Primary Examiner* — Victoria P Augustine
*Assistant Examiner* — Chad A Newton
(74) *Attorney, Agent, or Firm* — Klein, O'Neill & Singh, LLP

(57) ABSTRACT

The present disclosure provides systems and methods to aid in the resupply of product arrays, such as contact lenses. In an aspect, this is accomplished by providing a physical product array to a reseller. Additionally, a computer-operated application is provided that displays a virtual representation of the physical product array. The reseller can then manipulate the virtual storage array to more easily identify the specific product slots in the array that need to be restocked, and the application can interact directly with an ordering system for the product manufacturer to submit orders for fulfillment. In an aspect, the application stores the product attributes for each slot of the product array, so that a simple visual inspection of the physical array can be translated into the proper product without a reseller having to determine product attributes for the specific array slots.

17 Claims, 15 Drawing Sheets

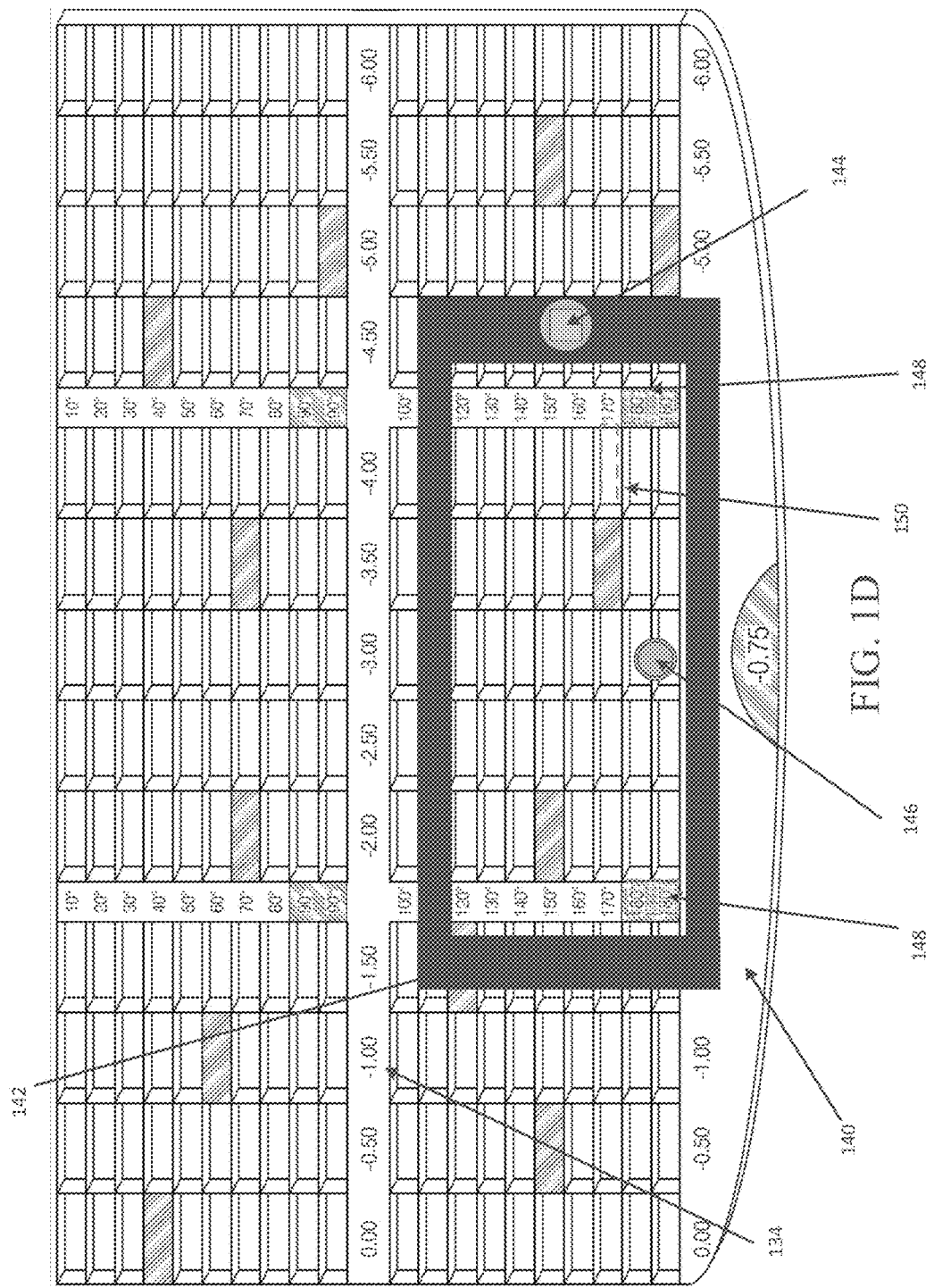

METHODS AND SYSTEMS FOR REPLENISHING SUPPLIES IN A PRODUCT ARRAY

CROSS-REFERENCE TO RELATED APPLICATION

This Application claims priority to provisional patent application Ser. No. 62/033,449, filed on Aug. 5, 2014, the entire contents of which are hereby incorporated by reference.

TECHNICAL FIELD

The present disclosure relates to product ordering methods and particularly to replenishing contact lens supplies.

BACKGROUND

Products with variability in multiple attributes, such as contact lenses, require supply sets with a large number of the variable attribute combinations ready and available to a potential customer to be most effective for the product manufacturer. If the correct combination of attributes is not available to the potential customer at the right time, there is a potential loss in sales, as the customer may turn to another brand that can meet their needs more immediately. For example, contact lenses come in a variety of types, such as hard and soft contacts; a variety of prescription powers; and other attributes (like cylinder power and axis measurements for toric lenses), just to name a few.

Often, a contact lens manufacturer will supply trial fit cases to optometrists and ophthalmologists that contain sample contact lenses that meet a wide range of these attribute combinations. With these fit cases, the doctor can select contacts with the proper prescription combination and let the patient try them immediately. However, patients are not typically willing to wait for their doctor to order contacts simply for a trial set that may or may not work. As such, if the doctor finds that a particular contact prescription is empty in a fit case, he or she is likely to just turn to another manufacturer's fit case. This will often result in a lost sale for the initial contact manufacturer, as patients are likely to proceed with the brand that they try. The patient may inherently believe that the selection is a recommendation of brand from their doctor, rather than what may simply be the result of poor supply in the test kit.

SUMMARY

The present disclosure provides systems and methods to aid in the resupply of product arrays. In an aspect, this is accomplished by providing a physical product array to a reseller. Additionally, a computer-operated application is provided that displays a virtual representation of the physical product array. The reseller or a sales representative can then manipulate the virtual storage array to more easily identify the specific product slots in the physical array that need to be restocked, and the application can interact directly with a manufacturer's or distributor's ordering system to submit orders for fulfillment. In an aspect, the application stores the product attributes for each slot of the product array, so that a simple visual inspection of the physical array can be translated into the proper product without a reseller or sales representative having to determine product attributes for the specific array slots.

This brief summary has been provided so that the nature of this disclosure may be understood quickly. A more complete understanding of the disclosure can be obtained by reference to the following detailed description of the various thereof in connection with the attached drawings.

BRIEF DESCRIPTION OF THE DRAWINGS

The foregoing features and other features will now be described with reference to the drawings of the various aspects. In the drawings, the same components have the same reference numerals. The illustrated aspects are intended to illustrate, but not to limit the present disclosure. The drawings include the following Figures:

FIGS. 1B-1D illustrate examples of ordering input methods according to aspects of the disclosure;

DETAILED DESCRIPTION

Figure 1:
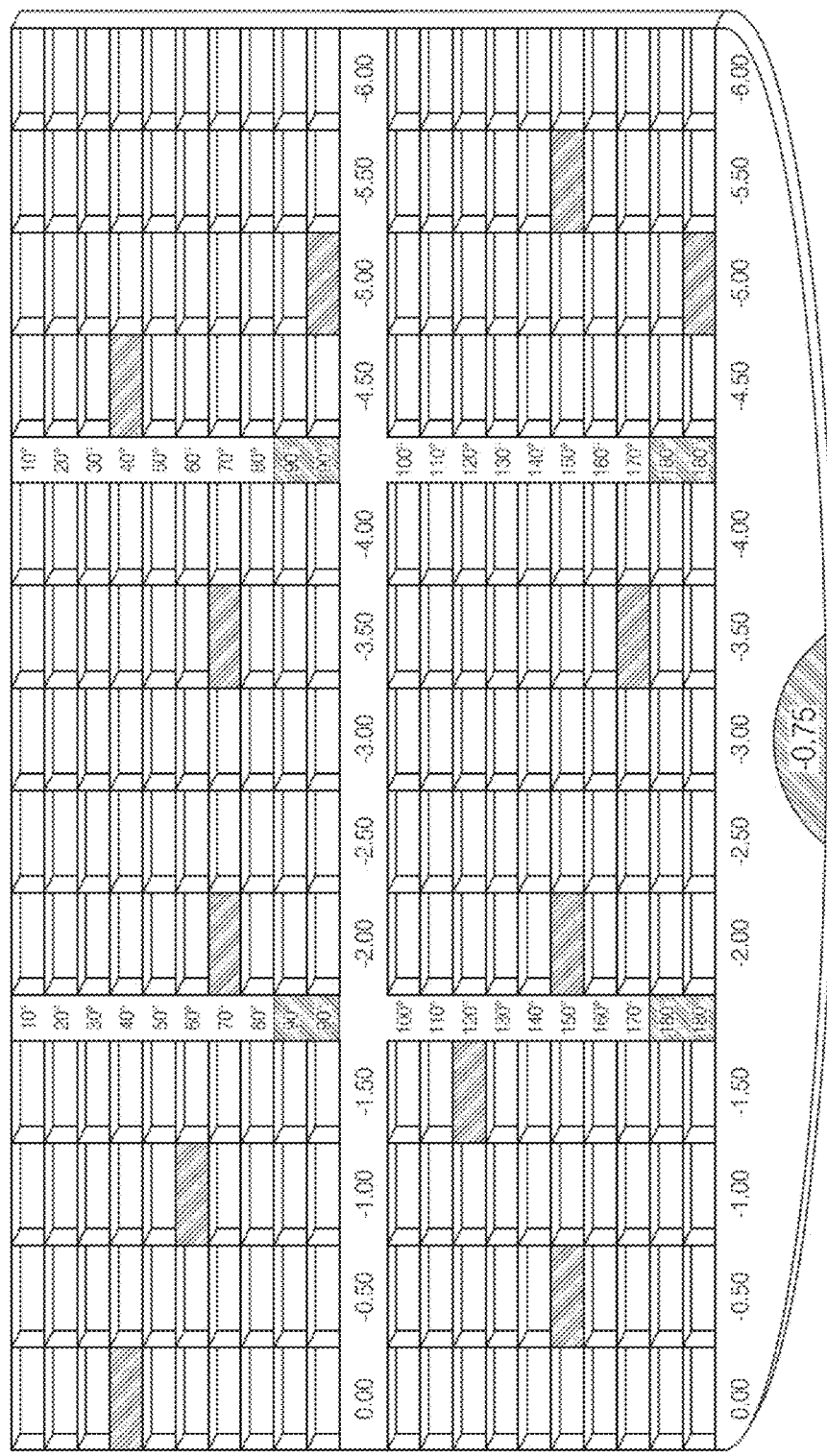
FIG. 1 illustrates an exemplary physical tray with a plurality of slots or storage spaces holding a supply of contact lenses having a variety of prescription variable combinations.

The following disclosure is directed to devices and methods for product ordering and particularly to replenishing contact lens supplies and packaged contact lenses forming said supplies. More particularly, the present devices and methods are directed to replenishing contact lens packages using both a digital image of an array of storage spaces and physical storage spaces. Devices and methods of the present disclosure can be used with lens packages having hydrogel contact lenses, including conventional hydrogel and silicone hydrogel contact lenses. The present devices and methods can be used with contact lenses formed using various methods known in the art, including cast molding, lathing, spin casting, etc.

As a preliminary note, the terms "component," "module," "system," and the like as used herein are intended to refer to a computer-related entity, such as a software-executing general purpose processor, hardware, firmware, and/or a combination thereof. For example, a component may be, but is not limited to being, a process running on a processor, a processor, an object, an executable, a thread of execution, a program, and/or a computer.

By way of illustration, both an application running on a server and the server can be a component. One or more components may reside within a process and/or thread of execution, and a component may be localized on one computer and/or distributed between two or more computers. Also, these components can execute from various non-transitory computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal).

Computer executable components can be stored, for example, at non-transitory, computer readable media including, but not limited to, an ASIC (application specific integrated circuit), CD (compact disc), DVD (digital video disk), ROM (read only memory), floppy disk, hard disk (HDD), solid state drive (SSD), EEPROM (electrically erasable programmable read only memory), memory stick or any other storage device, in accordance with the claimed subject matter.

Contact lens packages useable herein can include packages containing soft contact lenses. Contact lenses usable with the devices and methods disclosed herein include hydrogel contact lenses and any other contact lenses, as well as additional products. A silicone hydrogel contact lens is a hydrogel contact lens that comprises a silicone component. Examples of silicone hydrogel contact lenses that can be used with the present devices and methods include, but are not limited to, silicone hydrogel contact lenses having the following U.S. Adopted Names (USANs): lotrafilcon A, lotrafilcon B, balafilcon A, galyfilcon A, senofilcon A, comfilcon A, enfilcon A, and stenfilcon A. A non-silicone hydrogel contact lens is a hydrogel contact lens that is free of a silicone component. Examples of non-silicone hydrogel contact lenses that can be used with the present devices and methods include hydrogel contact lenses having the following USANs: omafilcon A, ocufilcon A, ocufilcon B, ocufilcon C, ocufilcon D, ocufilcon E, etafilcon A, methafilcon A, and methafilcon B, among others.

With reference now to FIG. 1, an exemplary physical tray having a plurality of storage spaces or slots holding a supply of contact lenses having a variety of prescription variable combinations is shown. Each storage space or slot can store one or more contact lens packages having the same prescription type. As illustrated, some of the highlighted slots are indicated to be full, while others are illustrated as empty. In this case, the tray houses a large number of toric contact lenses that vary based on cylinder power and degree axis of the toric optic zone—two variables for a toric lens prescription. As shown, this tray is arranged in a matrix with slots running along the X-axis varying based on sphere power (for example from 0.00 to −6.00 diopters (D)) and slots running along the Y-axis varying based on degrees (for example, from 10° to 180°). All of the lenses in this tray may relate to one contact lens cylinder power, as shown by the "−0.75" (−0.75 D) at the bottom of the tray. A full test kit may comprise numerous trays varying in cylinder power. Of course, similar test kits or product arrays may be arranged based on other product variables in keeping with the teachings herein. For example, a test kit can have an array of regular prescriptions while another test kit can include a combination of regular prescriptions and bifocals. In an aspect, the bottom of a slot may include a recognizable color or pattern that is preferably distinct from the tray or product packages (like contact lens packages) in order to provide a recognizable indication that a particular tray slot is empty.

Figure 1B:
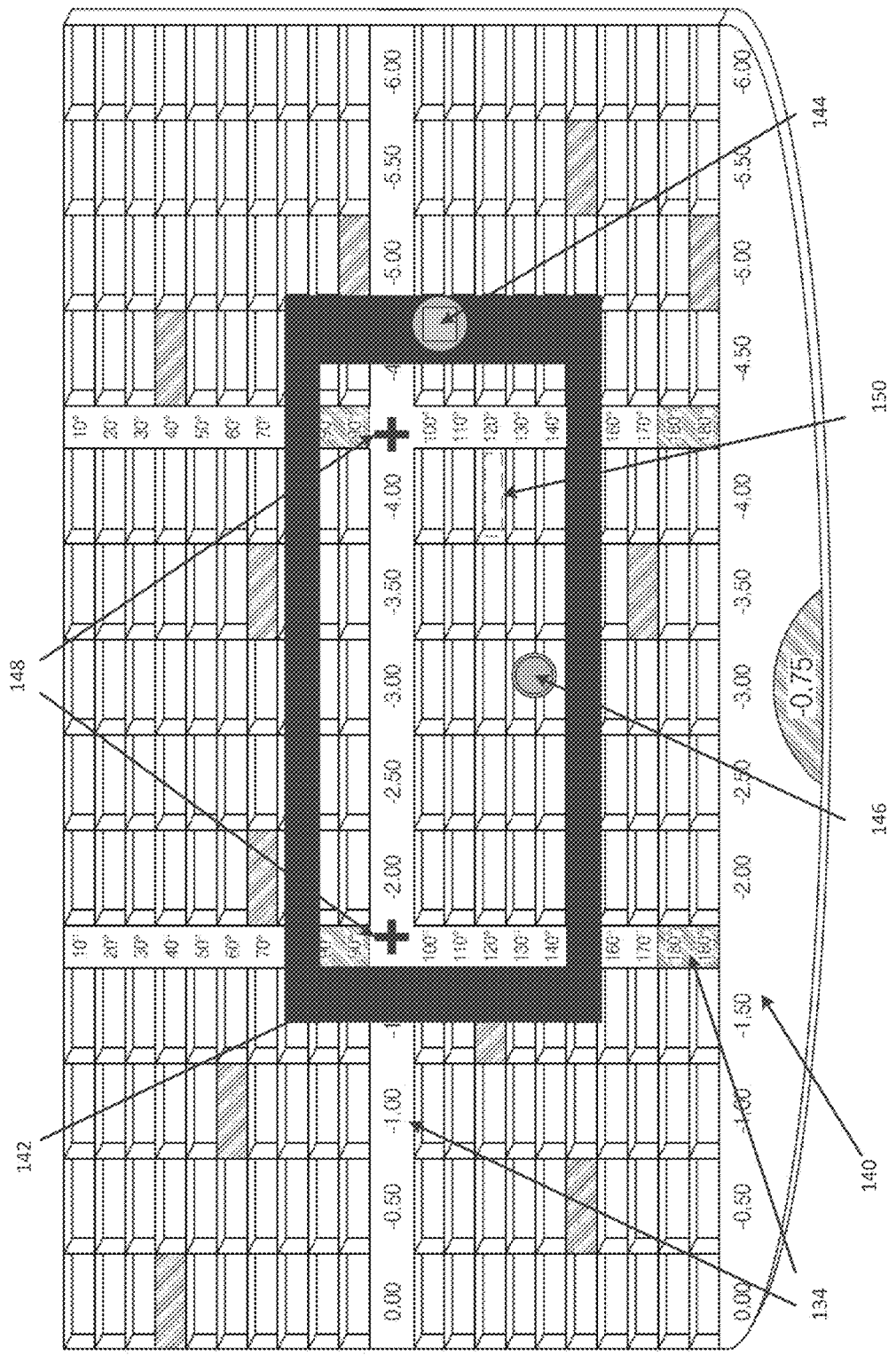

FIG. 1B illustrates an example input system for an ordering system as described herein. Illustrated in FIG. 1B is a product tray 140 as described above with respect to FIG. 1. The tray 240 is divided into a grid of product slots 150 by different product attribute designations 134, along the x- and y-axes. Additionally, in FIG. 1B, an ordering device 142 is illustrated, which may comprise a smart phone or tablet running an application (or app) for ordering product, for example. In other aspects, a laptop computer or other device may also be used. In an aspect, the device 142 runs an application that accepts input, at least in part, by using a camera feature of the device 142. In an aspect, the user can call up the camera feature on the display 144, which may include a view of what the device's camera sees and a virtual input button 146, such as to take a picture. In an aspect, the display 144 may also include placement indicators 148 (in this case crosshairs 148) that help the user and/or the application to determine the image's orientation with respect to the physical tray 140. For example, as illustrated in FIG. 1B, the display 142 may include crosses that a user can align with the tray 140 dividers. Once a picture is taken, the application can process the image to determine, for example, what product trays 150 are empty and preselect these products for ordering. As described above, an empty slot of a tray may include a particular color or pattern recognizable in image processing to more easily identify the empty slots. Alternatively, placement indicators are omitted and the user is allowed to freely capture any desired image of the product tray 140, such as using free form.

Figure 1C:
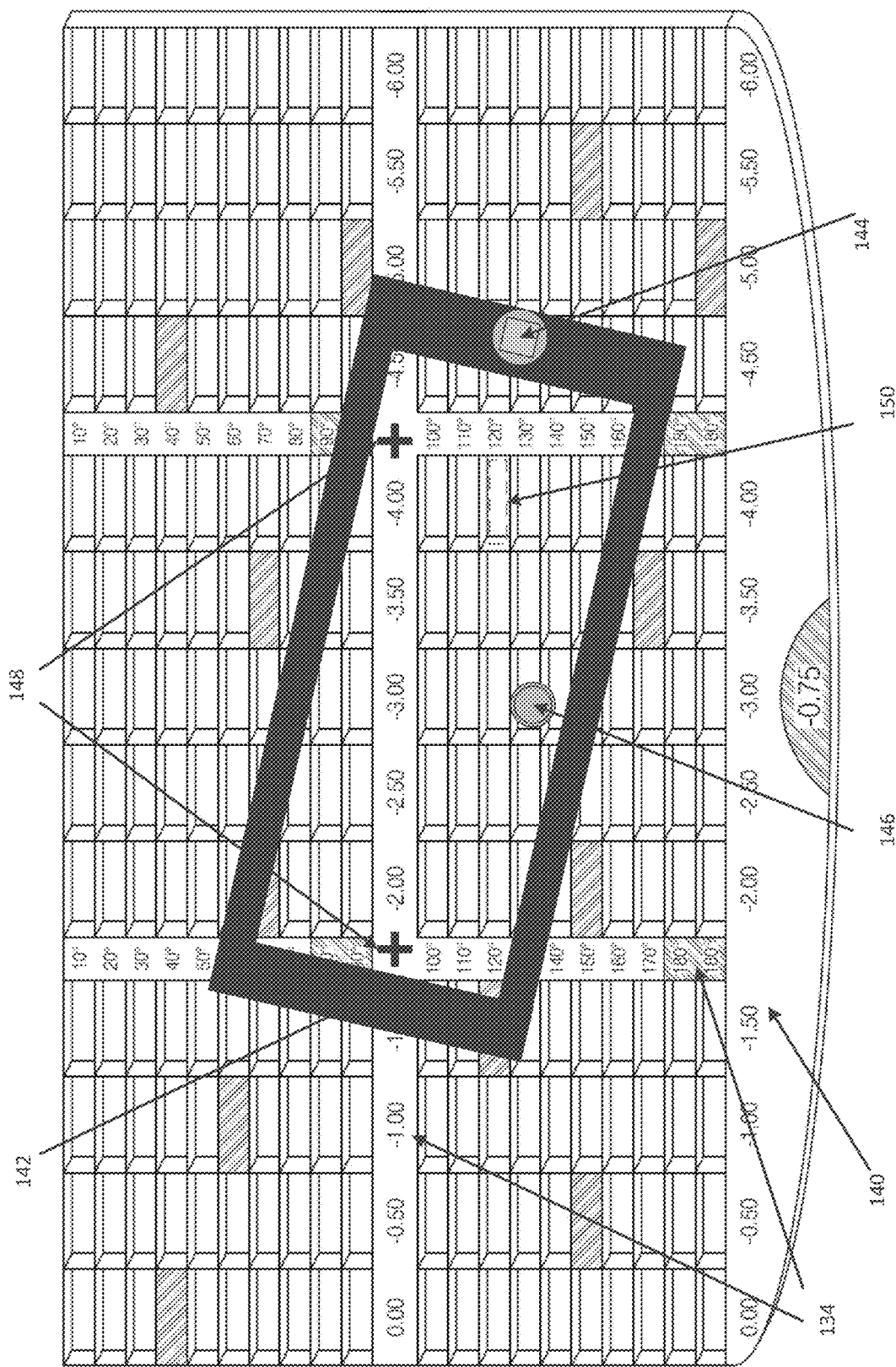

In another aspect, the application may attempt to process the camera input on the fly and display the placement indicators 148 in relation to a reference point or points on the physical product tray 140. An example of this is illustrated in FIG. 1C. This figure includes the same elements as FIG. 1B, but as indicated, the dynamic camera image is being processed while a user is moving the device 142, and the application displays the crosshairs 148 on or near reference points on the tray to help a user arrange the camera image appropriately. For example, in FIG. 1C the user's device 142 and thus the camera input are askew in relation to the tray, but the crosshairs 148 are correctly showing the intersections of primary tray dividers. In a dynamic processing of images such as this, the user may be able to better align the camera and device 142 to take an image of the desired section of the tray 140. In another aspect, the crosshairs may be included in the image taken, so that the image processing of the application can quickly orient the image to better detect the tray's various product slots 150.

FIG. 1D illustrates another example of a camera-based input with a physical tray 140 and a device 142. In an aspect as illustrated, the physical tray 140 may include tray location identifiers 152 (shown here as blue highlighted tray division indications). These tray location identifiers 152 may be used by the ordering application of the device 142 for image processing of the camera picture input. In an aspect, the application display may again include placement indicators 148 (shown here as box outlines to mirror the shape of the tray location identifiers 152) to assist a user in properly or best aligning the device's camera to capture input for the application. The processing of this input will be described in more detail below.

Figure 2:
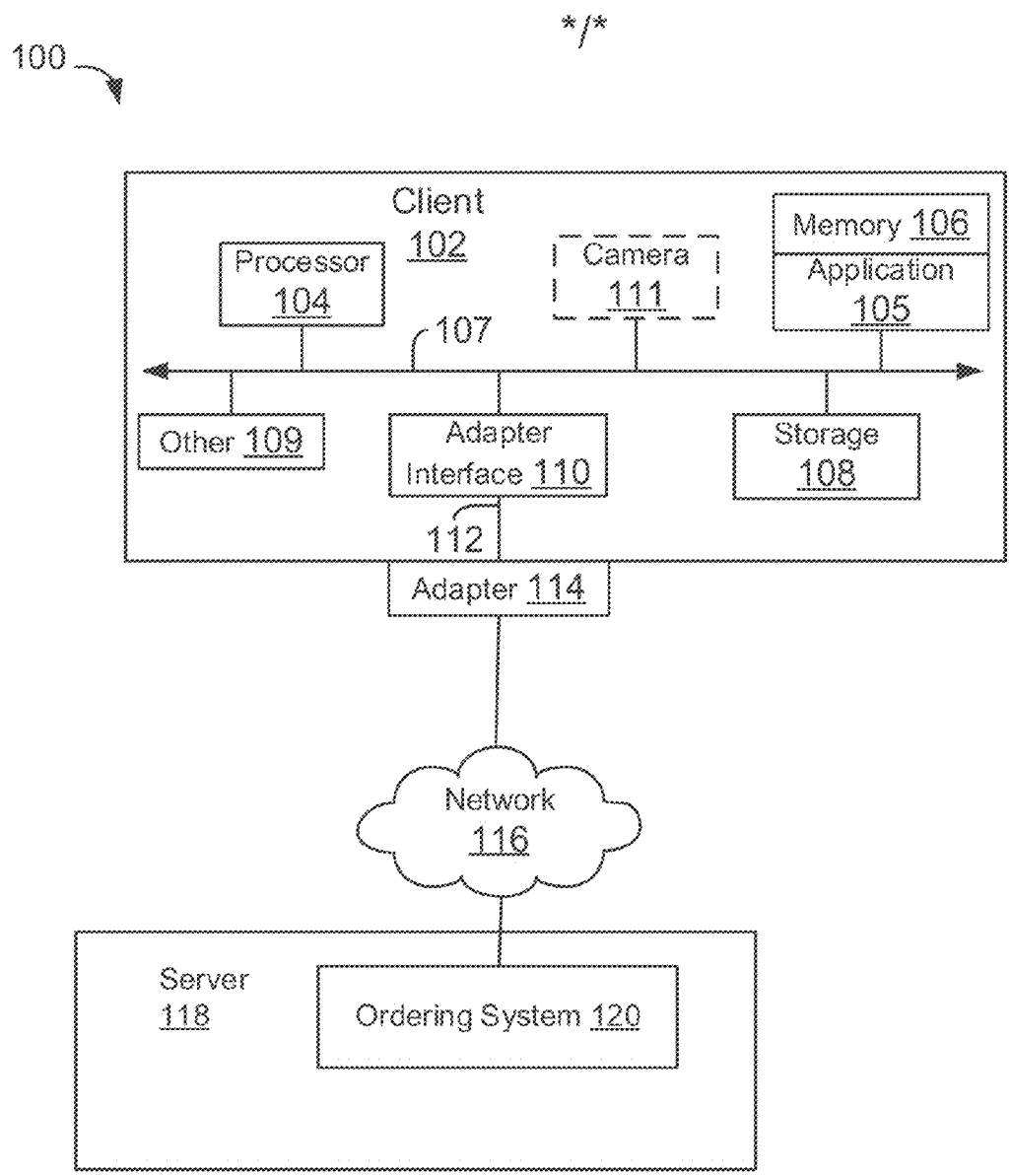
FIG. 2 illustrates an exemplary ordering system of an aspect of the present disclosure.

FIG. 2 illustrates a high level block diagram of an exemplary ordering system 100 for use with ordering items of a test kit, such as that described herein. Ordering system 100 includes a client device 102 that communicates with a server 118 through a network 116. A client device 102 may include any general purpose computing device capable of handling the processes described herein, including, for example, a tablet, a smartphone, a laptop or desktop computer, or the like.

In an aspect, a client device 102 includes a processor 104, a memory 106, a storage device 108, a display 109, and a network interface 110 which communicate through a bus system 107. Client 102 may further include other components (not shown), such as for input and output or communication, such as a mouse, keyboard, speakers, and the like. In another aspect, the client device 102 may further include a camera 111, such as a digital camera, although not all aspects may include or utilize this feature. While these other components may be of use, they are not in and of themselves particularly germane to the disclosure.

The bus system 107 shown is an abstraction that represents any one or more separate physical buses and/or point-to-point connections, connected by appropriate bridges, adapters and/or controllers. The bus system 107, therefore, may include, for example, a system bus, a Peripheral Component Interconnect (PCI) bus, a HyperTransport or industry standard architecture (ISA) bus, a small computer system interface (SCSI) bus, a universal serial bus (USB), or an Institute of Electrical and Electronics Engineers (IEEE) standard 1394 bus (sometimes referred to as "Firewire").

In an aspect, the processor 104 is a central processing unit (CPU) of the client device 102 and, thus, controls its overall operation. In certain aspects, the processor 104 accomplishes this by executing software stored in storage 108 and operated out of memory 106. A processor 104 may be, or may include, one or more programmable general-purpose or special-purpose microprocessors, digital signal processors (DSPs), programmable controllers, application specific integrated circuits (ASICs), programmable logic devices (PLDs), or the like, or a combination of such devices. The client device 102 may be a special purpose ordering device or may be a general purpose device with an operating system such as, for example, an appropriate version of Apple® iOS, Linux, Android™, or a Windows® OS.

Memory 106 represents any form of random access memory (RAM), read-only memory (ROM), flash memory, or the like, or a combination of such devices. Memory 106 includes the main memory of the client device 102. Application 105 that implements the process steps described herein may reside in and be executed (by processor 104) from memory 106.

Also connected to the processor 104 through the bus system 107 are one or more internal storage devices 108 and a network interface 110. Storage devices 108 may be, or may include any conventional medium for storing data in a non-volatile manner, such as one or more magnetic or optical based disks, a solid state drive, or the like. In another aspect, the application 105 is stored in storage 108 and called into memory 106 during operation. The network interface 110 provides the client device 102 with the ability to communicate with remote devices (e.g., storage servers) over a network and may be, for example, an Ethernet adapter, a Fibre Channel adapter, a wireless communications adapter, or the like.

According to an aspect, client 102 runs an application 105 for ordering items in a product array and may communicate, through network 116, with an ordering system 120 operating on server 118. Although not illustrated in detail, server 118 may include one or more general processing systems with basic components similar to client 102. In an aspect, server 118 includes one or more processors for carrying out an operating system and an ordering system 120 application.

In an aspect, application 105 may operate on a client device 102 and cause display 109 to present a virtual product tray to the user that mimics the physical tray provided to a reseller or brand representative, such as an optometrist's office.

Figure 3:
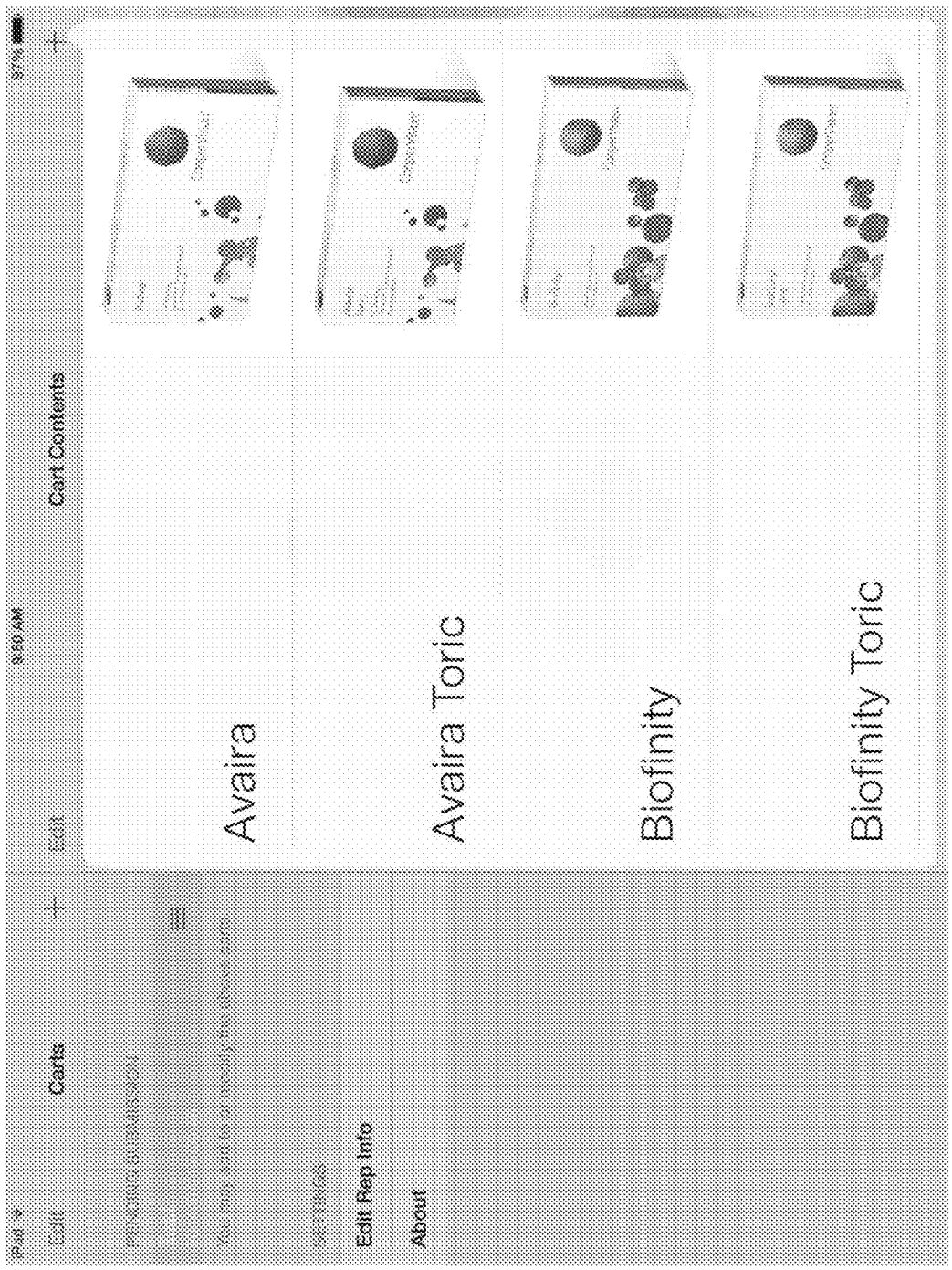
FIGS. 3-10 are exemplary screenshots of a client view of an ordering system application according to an aspect of the present disclosure.
Figure 4:
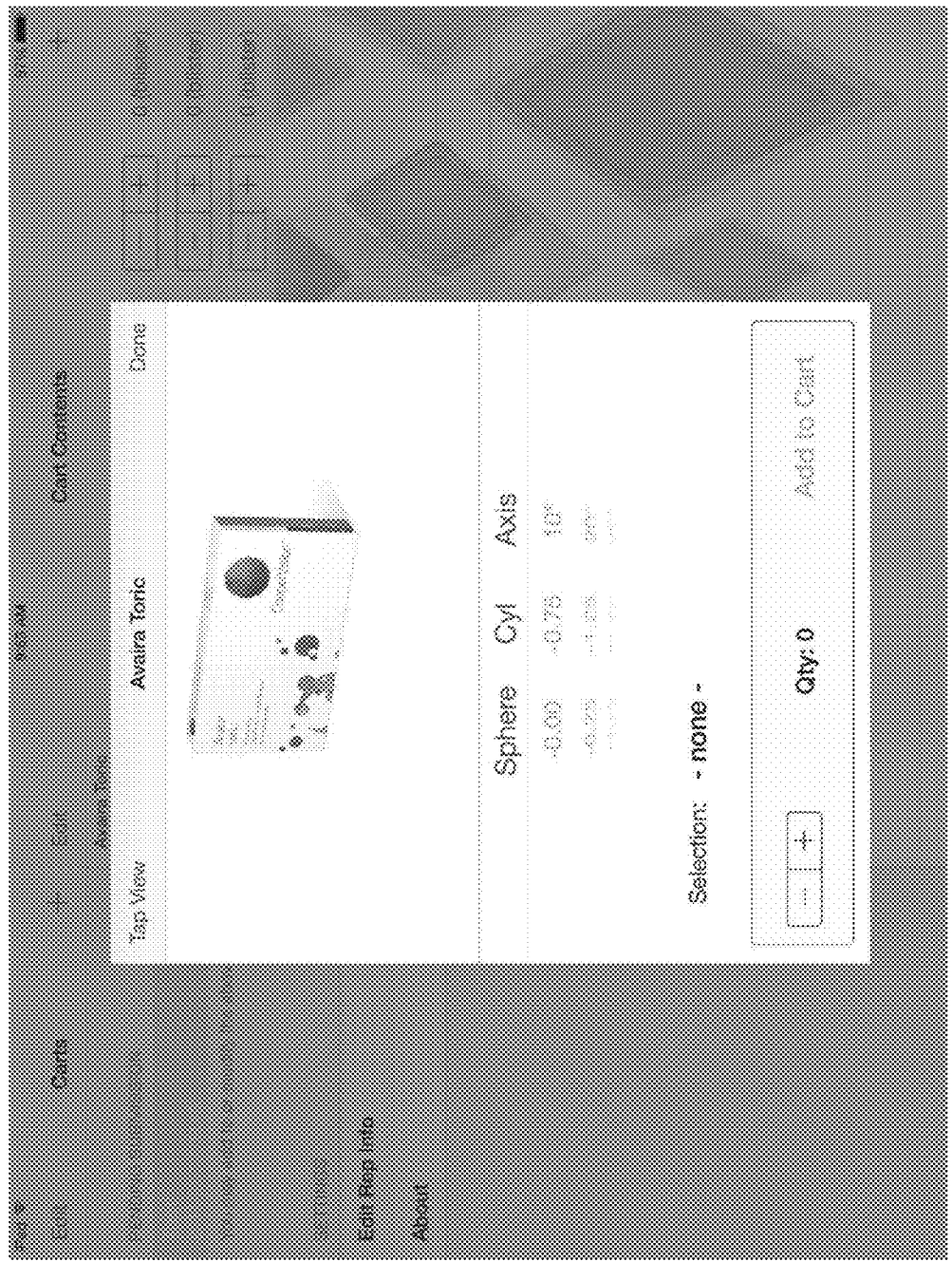
Figure 5:
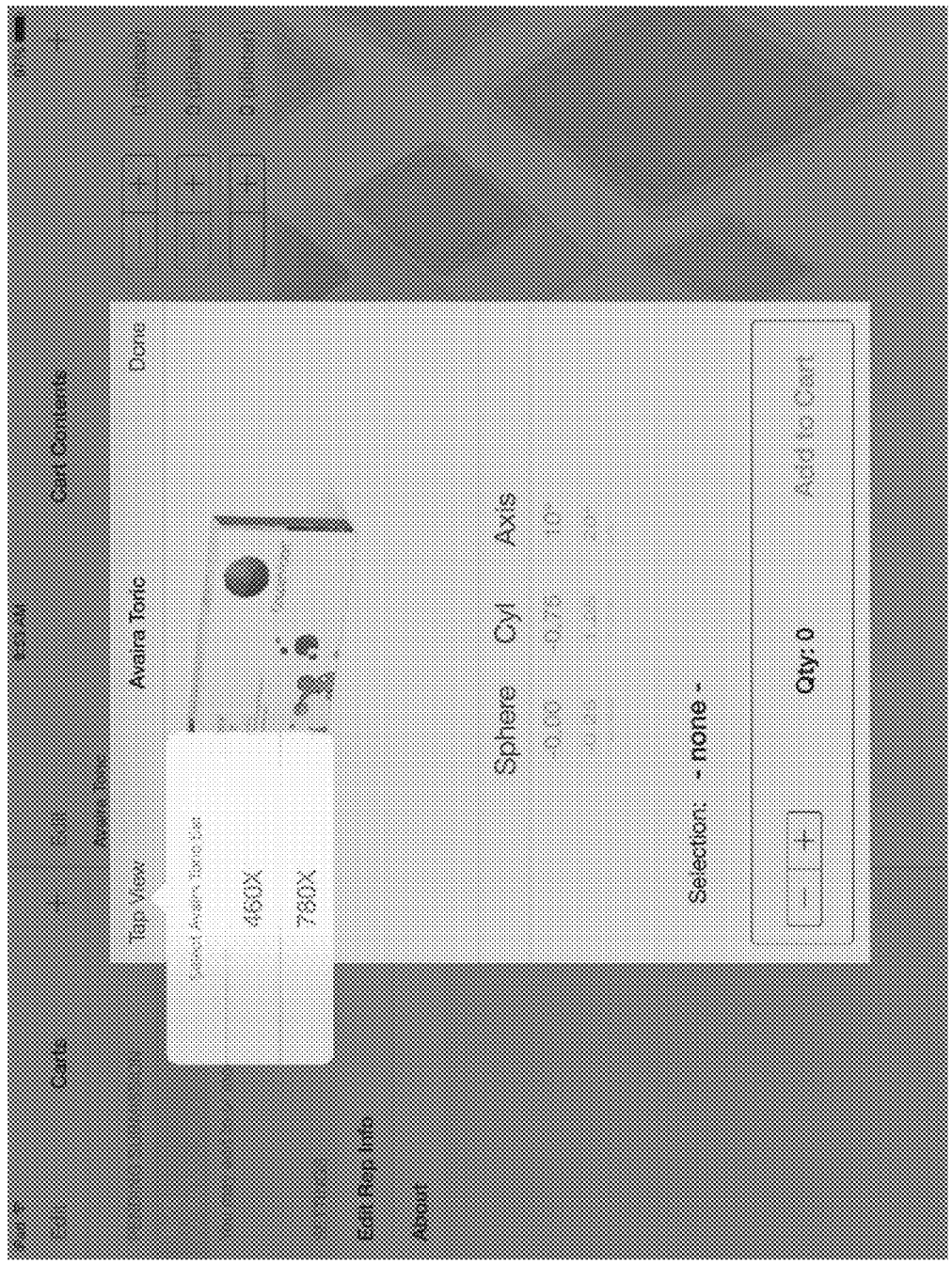

FIGS. 3 through 10 illustrate screenshots of an exemplary graphical user interface (GUI) presented by application 105. In an aspect, FIG. 3 illustrates an ordering page for selecting the specific brand of contact lenses. After selecting a brand, FIG. 4 illustrates an exemplary ordering page, where prescription elements can be selected in accordance with a first ordering view type or option. As shown, the user can select the quantity to be added to cart after selecting the desired corrective combinations by rotating the wheels or select the "Tap View" option to bring up the screen of FIG. 5, which allows the user to select a contact lens set. As shown, the options include a set containing 460 contact lens combinations or 780 lens combinations to match the corresponding physical tray. Choosing the set, such as 460 or 480, then brings up FIG. 6, which allows the user to select a drawer corresponding to a desired cylinder power. After selecting the drawer, FIG. 7 appears and illustrates the virtual tray ordering method described herein.

Figure 6:
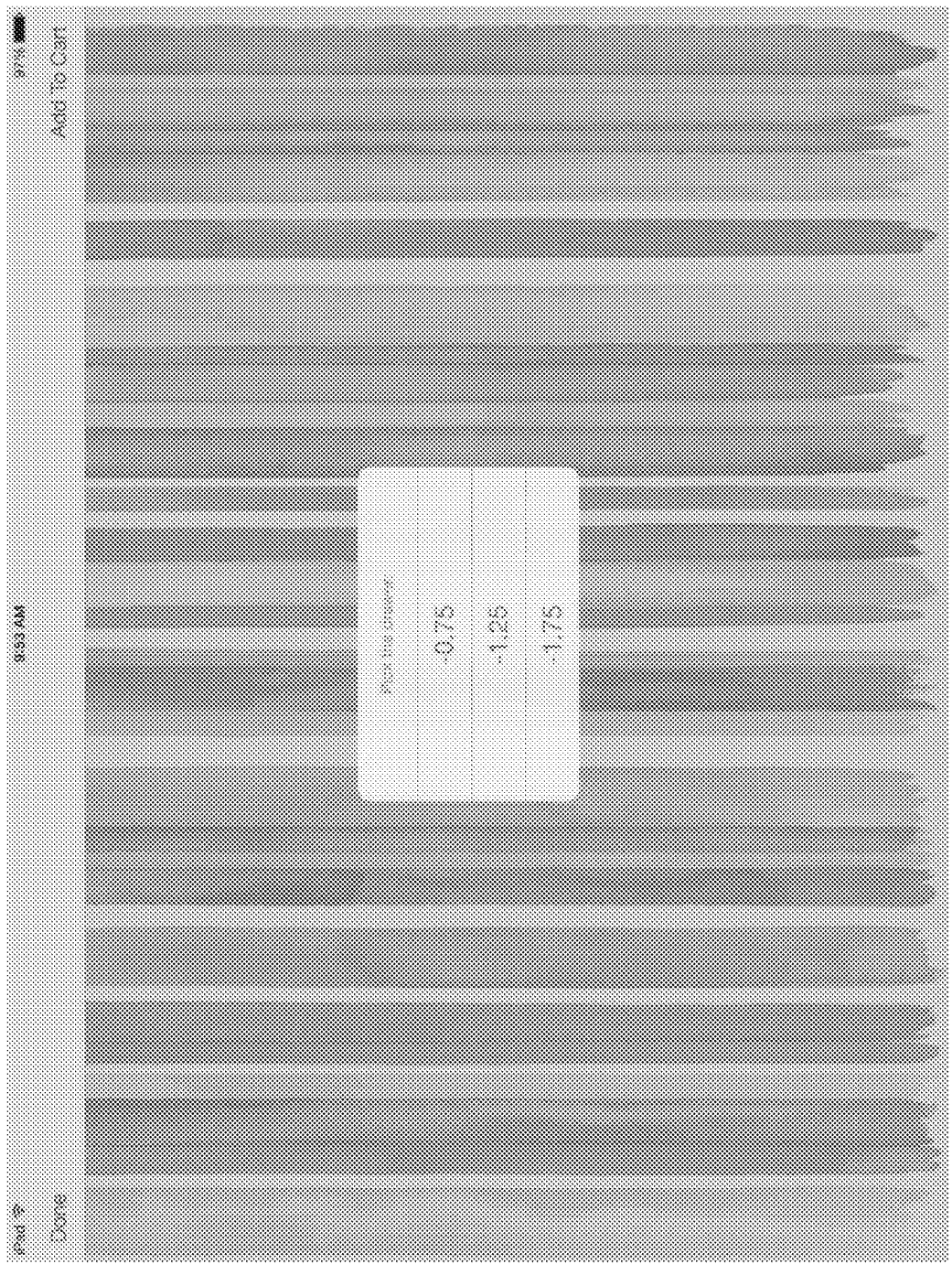
Figure 7:
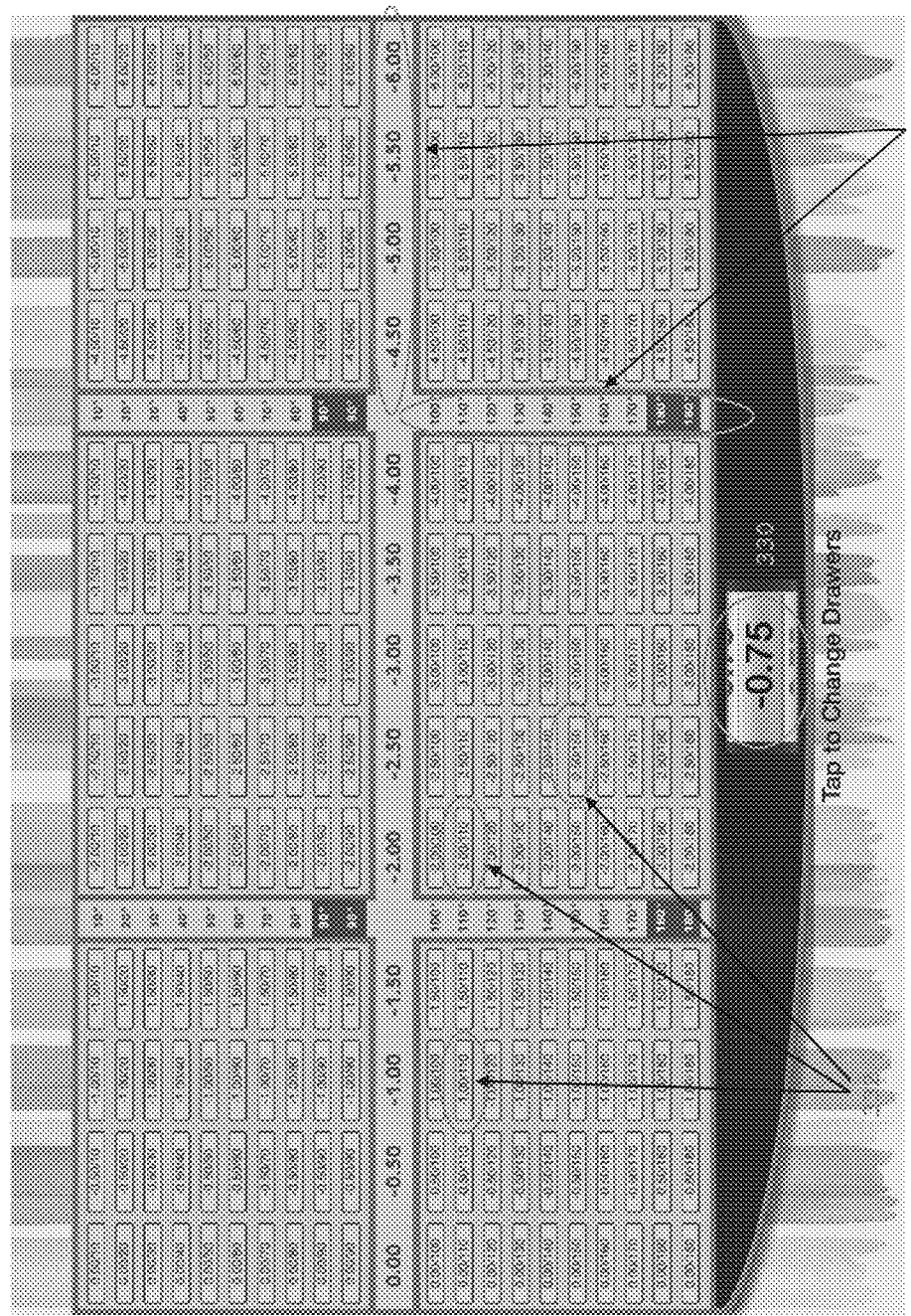

As illustrated in FIG. 7, application 105 may include a tray or drawer selector 330 that allows the user to see each of a plurality of drawers (similar to the drawer selection of FIG. 6). Tray selector 330 may include a scroll wheel, a tab selector, radio buttons, or any of a number of other appropriate input methods known to those of skill in the art. In an aspect, tray selector 330 lists tray options by, for example, contact lens power, such as a cylinder power.

Rather than including slots for product storage, such as in the physical tray of FIG. 1, the virtual product tray of FIG. 7 includes, in an aspect, an array of virtual product tray slots 332. In an aspect, the virtual slots 332 comprise buttons that a user may operate to select one or more slots for ordering one or more contact lenses having prescriptions that match the selected slots. Preferably, each slot of the physical tray has a counterpart button, selectable box, checkbox, radio button, or other suitable selection tool in the virtual tray. This allows a user to eye-ball the physical tray for slots for which to order contact lenses, such as to visually select which slots of the tray may be empty, and then match the slots with the virtual tray shown in FIG. 7. Once again, virtual product tray slots 332 may comprise any of a variety of different interactive software elements, such as buttons, check boxes, drop down boxes, and the like.

In order to help orientate a user, the application 105 may further include representations of the property identifiers 334 that help the same user find the proper product based on attribute combinations in the physical tray. Additionally, in an aspect, application 105 may allow a user to "pinch and widen" their view of the virtual tray to better see different portions of it. In another aspect, a user may scroll through different portions of a virtual tray or the like. As such, the property identifiers 334 may further orient a user when they are only looking at a portion of the virtual tray.

More specifically, in an aspect of the disclosure as shown, FIG. 1 illustrates a contact lens tray that is organized by various toric contact lens prescription elements, and FIG. 7 illustrates a GUI presented by application 105 that provides a virtual tray representing the same toric contact lens prescription element layout.

It is important to note, that the various prescription elements could be organized differently without detracting from the teachings of the disclosure herein. For example, trays could be separated by degree of axis, with the sphere power and cylinder power measurements, being represented in the x- and y-axes. Other nonprescription elements could also be used for categorizations, including for example, lens tint for cosmetic eye color changes, and the like.

Figure 8:
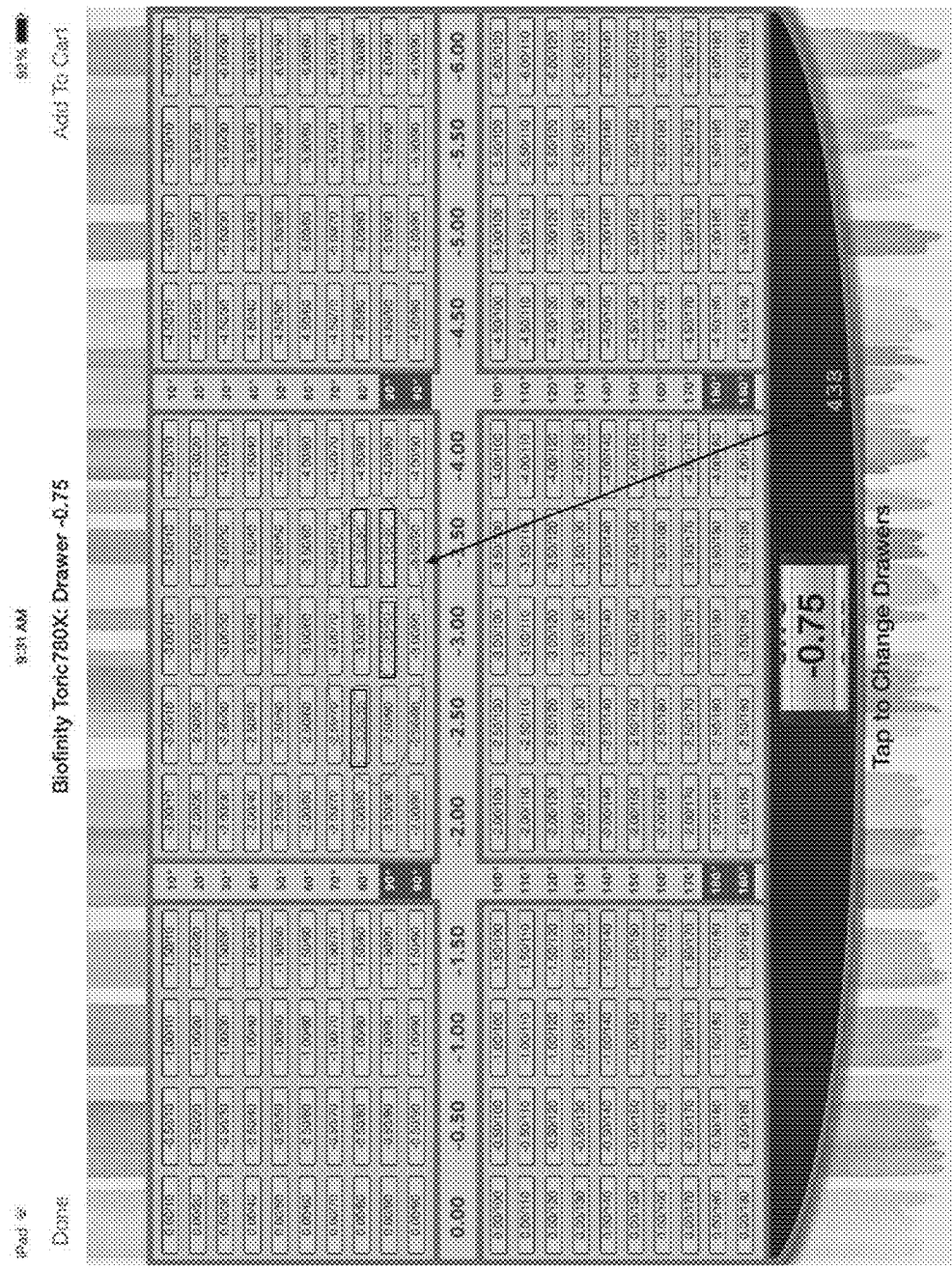
Figure 9:
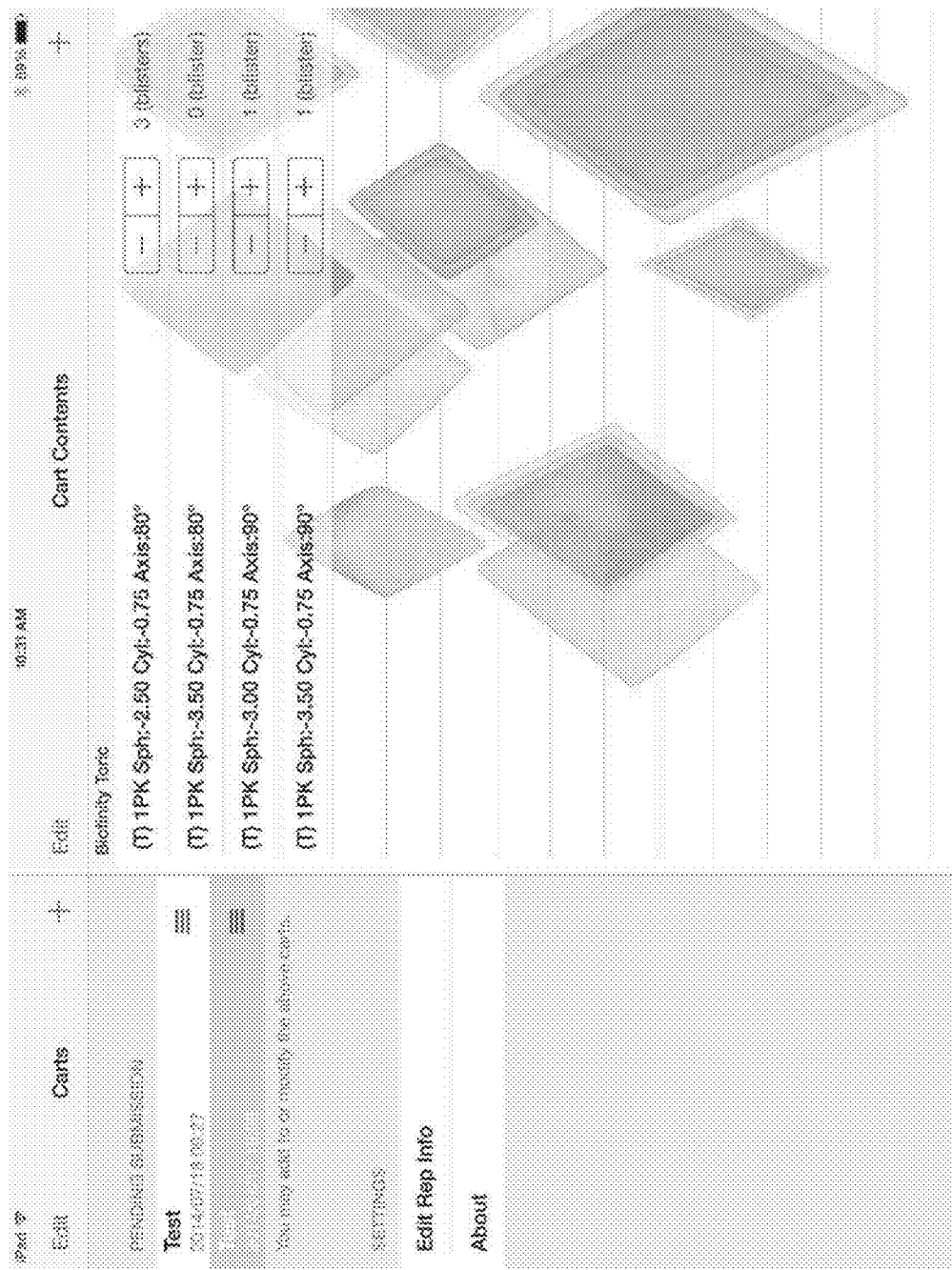

In an aspect, a user of application 105 selects the different buttons 332 representing the product combinations that they wish to order. An example of this selection is illustrated in FIG. 8, where four different products are selected for ordering (product array selections 438). In an aspect, a user may select and deselect as many different buttons as the user desires for ordering, and may then click an "Add to Cart" button or similarly indicate that he or she has made the desired selections for ordering. In an aspect, a submission screen may allow a user to input the quantity of a selection for ordering and confirm the selections of the prior screen. In one aspect, a user may be presented with a summary or "shopping cart" screen, such as illustrated in FIG. 9. In an aspect, a minimum quantity (such as one) for each selection 438 may be assumed. As shown, however, a user can alter the ordering quantity, such as through −/+ buttons or the like. In another aspect, a separate screen for each product array selection 438 of FIG. 8 may be presented to the user one after another seeking confirmation and/or desired order quantities before going to a "shopping cart"-like screen. Additionally, when an order is complete, the user can submit it to the ordering system (see FIG. 10).

In an aspect, all of the ordering information is sent to the ordering system 120 (FIG. 2) for processing. In an alternative aspect, application 105 generates an email or other communication with the ordering information that the user supplied in the application 105. The email is then sent to the contact lens supplier or distributor, which then processes the order.

Figure 10:
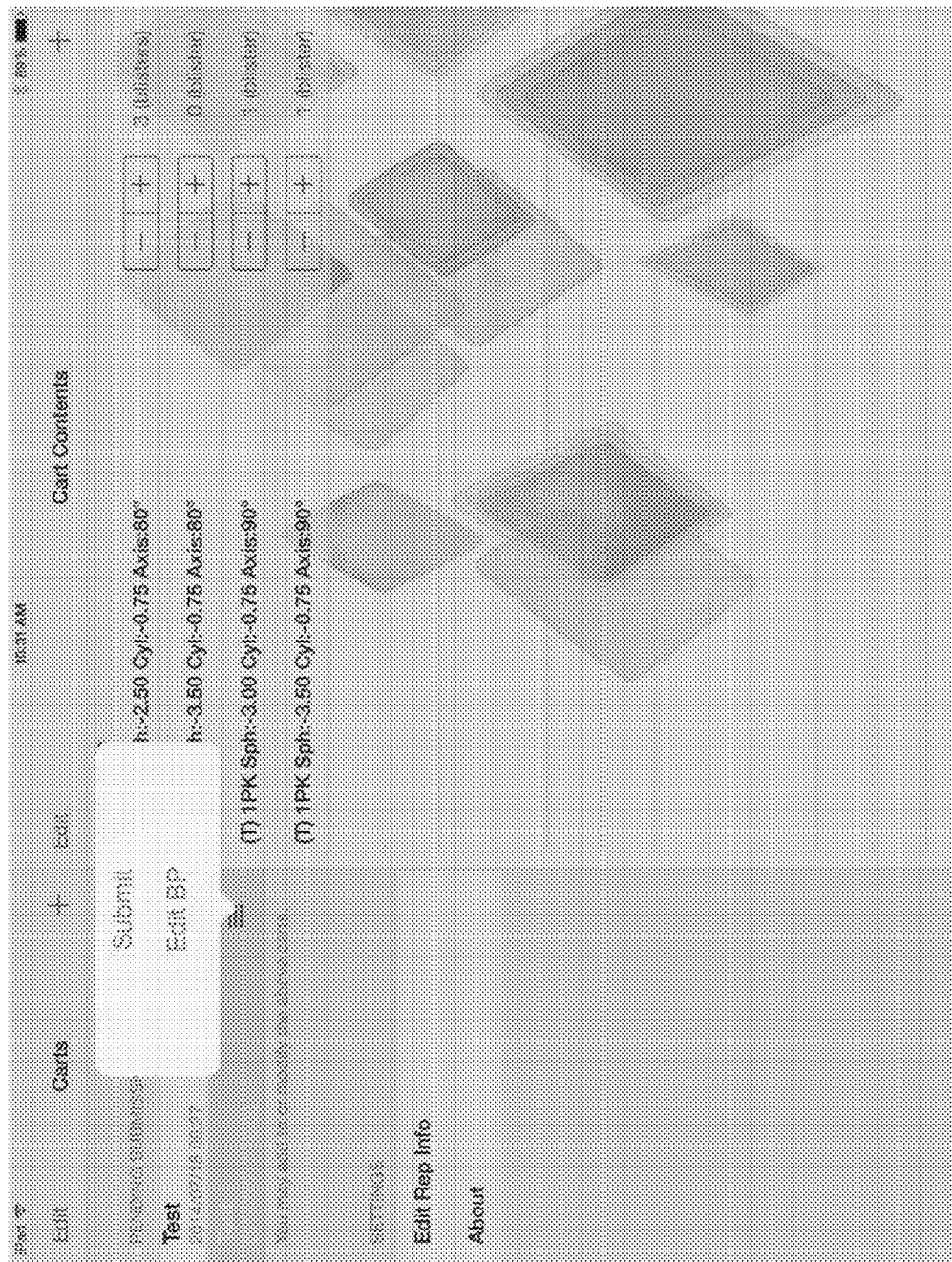
Figure 11:
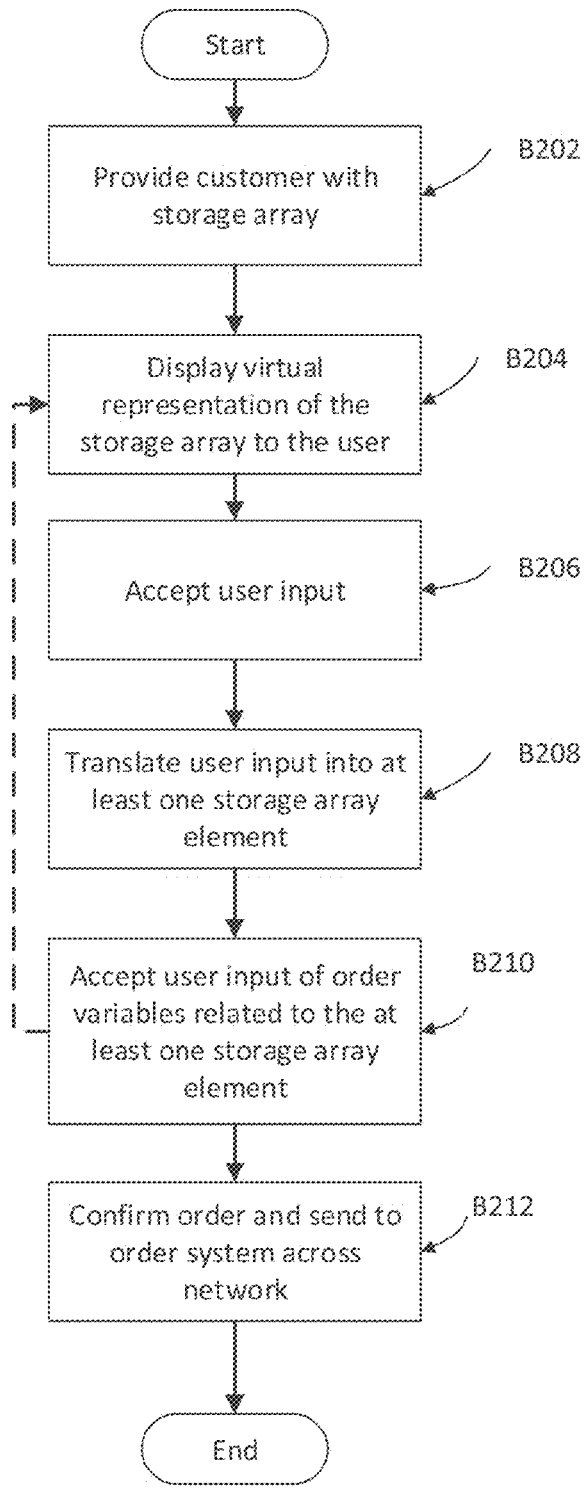
FIG. 11 shows an exemplary flow diagram for fulfilling an order according to an aspect.

While described generally with respect to the screenshots above, a process according to an aspect of the disclosure, is described with respect to FIG. 11. At block B202, the eye care practitioner, such as an optometrist's office, is provided with a physical product array, such as a set of trays including contact lens samples (FIG. 1). At block B204, a virtual representation of the product array (FIG. 7) is presented to the sales representative, such as when a contact lens sales representative calls up an ordering application on his or her tablet or smart phone. At block B206, user input is accepted, for example, by the application. As described, this may include selecting virtual representations of tray slots that correspond to empty or nearly empty physical tray slots (FIG. 8). At block B208, the user input is translated into at least one storage array element, such as by the application. For example, the application may determine what product attributes correspond to the virtual tray or button selected and may populate that information into an order form. At block B210, the application also accepts user input of order variables for the selected virtual tray. In an aspect, for example, the user may further select an order quantity and may select other variables related to the product if desired (FIG. 9). At block B212, the application confirms the order with the user and sends the order data across a network to an ordering system for order fulfillment (FIG. 10). This can be done while at the eye care practitioner's office, or at a later time when convenient.

Further exemplary aspects of the disclosure will now be described. In an aspect, client system 102 comprises an iPhone® or iPad® available from Apple® and runs an application 105 (or an "app"), which may, for example, be downloaded from the Apple App Store. Similarly, client system 102 may comprise an Android-based smart phone, tablet, or similar device. Moreover, in an aspect, the virtual product tray may be generated by application 105 with assistance from a camera 111 input from client system 102. Appropriate image processing software (as a part of or in addition to application 105, for example) may be used to identify the physical tray of interest to a user and/or identify empty slots for "preselection" by the application 105, for example. In such an aspect, application 105 may accept imaging input, process empty slots and display a tray with already selected slots (like FIG. 8) for which a user may be interested in ordering. In another aspect, image processing may be offloaded to server 118 with image data being forwarded over network 116 for processing and indications of possible ordering data being returned to application 105 over the network.

Figure 12:
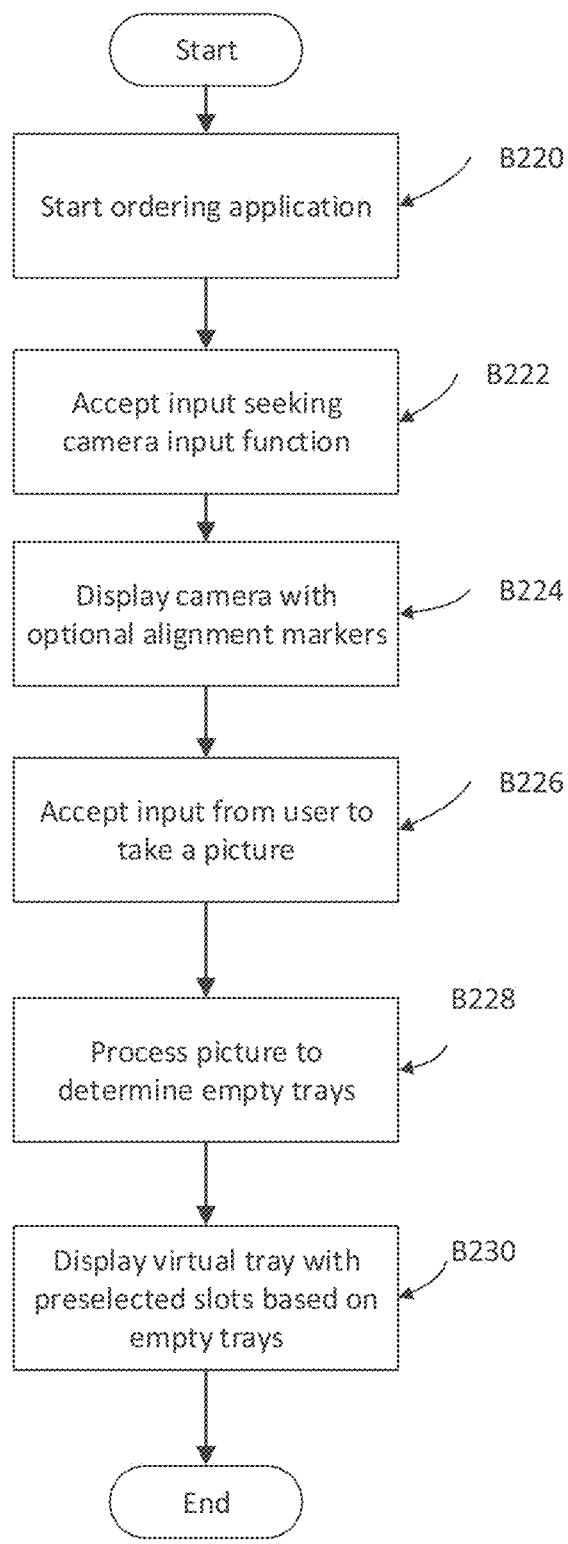
FIG. 12 shows an exemplary flow diagram for fulfilling an order according to another aspect.

Turning to FIG. 12, an example input method for an ordering system 100 that utilizes image processing (FIG. 2) is described. At block B220, an ordering application is started (on a client system 102, such as a smart phone or tablet). At block B222, a user provides input to the application that he or she wishes to use the camera to input order information. The application accepts this input and displays an image from the camera and/or otherwise provides a way for the user to capture an image of all or a portion of a physical tray of products. In an aspect, the display may also include placement indicators 148 (FIGS. 1B-1D) to help the user align the camera image with the physical tray.

At block B226, the application accepts input that the user has taken the picture and saves the image for processing. At block B228, the application processes the image to locate empty or partially empty trays and translates those locations into product types that correspond to that tray. In an aspect, this may include text recognition software for the product attribute designations 134. However, in other aspects, the approximate location compared to one or more tray location identifiers 152 (FIG. 1D) may be used to identify product slots. In an aspect, the application maintains a data structure that represents the product attributes of the products designed to be in each slot of a physical tray 140. In an aspect, the application can then display a virtual tray representation with the identified slots already highlighted (as in FIG. 8).

It is also important to note that, while exemplary embodiments were described with respect to contact lens fitting sets, the ideas described herein are applicable to a wide range of products, particularly those with wide variations within two or more attributes.

Thus, methods and systems for replenishing goods stored in an array, such as contact lens trial sets, have been described. Note that references throughout this specification to "one aspect" or "an aspect" mean that a particular feature, structure or characteristic described in connection with the aspect is included in at least one aspect of the present disclosure. Therefore, it is emphasized and should be appreciated that two or more references to "an aspect" or "one aspect" or "an alternative aspect" in various portions of this specification are not necessarily all referring to the same aspect. Furthermore, the particular features, structures or characteristics being referred to may be combined as suitable in one or more aspects of the disclosure, as will be recognized by those of ordinary skill in the art.

While the present disclosure is described above with respect to what is currently considered its preferred aspects, it is to be understood that the disclosure is not limited to that described above. To the contrary, the disclosure is intended to cover various modifications and equivalent arrangements within the spirit and scope of the appended claims.

What is claimed is:

1. A method comprising:
    displaying a digital image of an array of storage spaces on a client device having a screen to display the digital image of the array of storage spaces, wherein each storage space of the digital image of the array of storage spaces represents a contact lens prescription for a contact lens;
    placing at least a three by three array of the digital image of the array of storage spaces displayed on the client device in a same general space as a three by three array of physical storage spaces so that the digital image of the array of storage spaces and the array of physical storage spaces may be viewed by a user, wherein each physical storage space is sized and shaped to store at least one contact lens package having a contact lens prescription and wherein the contact lens prescription of each storage space of the digital image of the array of storage spaces corresponds to the contact lens prescription of a contact lens for each corresponding storage space in the three by three array of physical storage spaces;

receiving, in the client device, a selection of a chosen storage space within the three by three array of the digital image of the array of storage spaces that corresponds to an empty storage space within the three by three array of the physical array of storage spaces, said selecting of the empty storage space defining a first order selection;

receiving, in the client device, an input of a number that corresponds to a quantity of contact lens packages to order for the first order selection; and confirming an order in a shopping cart using the client device.

2. The method of claim 1 wherein the receiving of the selection of the chosen storage space within the three by three array of the digital image of the array of storage spaces comprises taking an image of the three by three array of physical storage spaces using an image capture device associated with the client device and processing the image to locate an empty storage space using the client device.

3. The method of claim 1 further comprising: sending the order from the client device across a network to an ordering system.

4. The method of claim 1 wherein receiving of a selection of the selected storage space comprises receiving, in the client device, a selection of a virtual button displayed on the screen of the client device that is associated with one of the storage spaces of the three by three array of the digital image of the array of storage space.

5. The method of claim 4 wherein the screen of the client device comprises a touch screen and the selecting the virtual button comprises processing input from the touch screen indicating the selection of the virtual button using the client device.

6. The method of claim 1, wherein the digital image of an array of storage spaces corresponds to spaces for a specific product name from a specific contact lens manufacturer.

7. A non-transitory, machine readable storage medium having stored thereon instructions for performing a method, comprising machine executable code which when executed by at least one machine, causes the machine to:

capture an image of a portion of a physical storage tray that includes a plurality of storage slots, each of the plurality of storage slots of the physical tray sized and shaped to store at least one product with a particular set of attributes, said plurality of storage slots including a first storage slot, a second storage slot, and a third storage slot;

present, to a user, a digital image of a virtual storage tray with a plurality of storage slots, the digital image of the virtual storage tray corresponding to the physical storage tray captured in the image and includes the first storage slot, the second storage slot and the third storage slot;

process the image of the physical tray to determine the particular set of attributes of the at least one product stored in each of the first, second, and third storage slots of the portion of the physical storage tray that has been imaged, the particular set of attributes of each of the first, second, and third storage slots being based on indicia associated with the physical tray;

accept input from a user indicative of selecting at least one of the first, second and third storage slots from the plurality of storage slots from the digital image of the virtual storage tray;

process the user input to determine at least one-set of attributes of the at least one product selected for ordering based on the particular set of attributes of the at least one product stored in the one of the plurality of storage slots of the physical storage tray that corresponds to the selected one of the first, second and third storage slots;

accept order data for an order of the at least one product corresponding to the selected one of the first, second and third storage slots; and send the order, over a network, representing the at least one set of attributes and the order quantity.

8. The machine readable storage medium of claim 7 wherein the plurality of storage slots in the physical storage tray stores contact lens samples.

9. The machine readable storage medium of claim 7 wherein sending an order comprises generating an email to a brand representative.

10. The machine readable storage medium of claim 7 wherein accepting order data comprises accepting order quantity information.

11. The machine readable storage medium of claim 7 wherein accepting order data comprises accepting payment information.

12. A system comprising:
a display;
a memory containing machine readable non-transitory medium comprising machine executable code having stored thereon instructions; and
a processor module coupled to the memory, the processor module configured to execute the machine executable code to:
present, through the display, a digital storage array image, the digital storage array image corresponding to a physical storage tray, wherein the physical storage tray includes a plurality of storage slots for storing contact lens packages that vary by one or more attributes, each of the plurality of storage slots storing contact lens packages with a particular attribute combination;
accept input from a user indicative of selecting a digital storage slot from the digital storage array image;
process the user input to determine at least one particular attribute combination of the contact lens packages selected for ordering without the user having to input the product attribute combination directly;
accept order data; and
send an order, over a network, representing the at least one particular attribute combination and the order quantity.

13. The system of claim 12 wherein the one or more attributes comprise: power, cylinder, and degree measurements.

14. The system of claim 12 wherein the display comprises a touch screen and the processor module configured to execute the machine executable code to is further configured to accept data from the touch screen indicative of the user input.

15. The system of claim 12 further comprising a camera and wherein the user input comprises capturing an image of the physical storage tray.

16. The system of claim 15 further comprising a network connection and wherein the processor module is further configured to execute machine executable code to:
   send the image from the camera, over the network, to an image processing program of an ordering system; and
   receive preliminary selections of at least one particular attribute combination for ordering without the user having to input the at least one particular attribute combination directly.

17. The system of claim 15 wherein the processor module is further configured to execute machine executable code to:
   process the image to determine a preliminary selection of at least one particular attribute combination for ordering without the user having to input the attribute combination directly.

* * * * *